United States Patent [19]

Murdoch et al.

[11] Patent Number: 5,362,373
[45] Date of Patent: Nov. 8, 1994

[54] OXYGEN AND METHANE PRODUCTION DEVICE

[75] Inventors: Karen E. Murdoch, Manchester; Philip J. Birbara, Windsor Locks, both of Conn.

[73] Assignee: United Technologies Corporation, Hartford, Conn.

[21] Appl. No.: 91,080

[22] Filed: Jul. 13, 1993

Related U.S. Application Data

[60] Continuation of Ser. No. 837,127, Mar. 13, 1992, abandoned, which is a division of Ser. No. 777,969, Oct. 17, 1991, Pat. No. 5,128,003.

[51] Int. Cl.$^5$ ............................................. C25B 9/00
[52] U.S. Cl. ................................... 204/242; 422/186; 422/189; 422/234; 422/305
[58] Field of Search ............... 204/242; 422/189, 234, 422/186, 305, 186.03

[56] References Cited

U.S. PATENT DOCUMENTS

| | | | |
|---|---|---|---|
| 3,873,328 | 3/1975 | Brueggemann et al. | 106/39.6 |
| 4,265,868 | 5/1981 | Kamody | 423/415 A |
| 4,410,504 | 10/1983 | Galasso et al. | 423/453 |
| 4,452,676 | 6/1984 | Birbara et al. | 204/129 |
| 4,836,898 | 6/1989 | Noyes | 204/129 |

OTHER PUBLICATIONS

Kiyoshi Otsuka, et al., "Steam Reborming of Hydrocarbons and Water Gas Shift Reaction Through a Way of Stabilized Zirconia Used as Hydrogen Separator", The Chemical Society of Japan, vol. 57, No. 11, (1984), pp. 3286–3289.

Gary Noyes, "Carbon Dioxide Reduction Process for Spacecraft ECLSS: A Comprehensive Review", Society of Automotive Engineers, Inc. (1988).

G. Noyes, et al., "Formation of Dense Carbon on Fused-Quartz Wool for Spacecraft Life Support Application", Advanced Ceramic Materials, vol. 1, No. 2, (1986), pp. 145–149.

S. K. Gangwal, et al., "The Catalysis of the Water Gas Shift Reaction on a Subbituminous Coal Char", pp. 603–607.

Hamilton Standard, "Sabatier Carbon Dioxide Reduction System for the Environmental Control and Life Support System Technology Demonstrator", vol. 1, Technical/Management, pp. 1–23–1–28, 2–1–2–81, Jan. 1987.

David L. Trimm, "Fundamental Aspects of the Formation and Gasification of Coke", Pyrolysis: Theory and Industrial, Practice, (1983), pp. 203–243.

Primary Examiner—Kathryn Gorgos
Attorney, Agent, or Firm—Mary R. Bonzagni

[57] ABSTRACT

A system for producing oxygen and methane. This system comprises a methanation reactor for reacting carbon dioxide and hydrogen to produce methane and water, a reforming reactor for reforming the water and methane to hydrogen and carbon monoxide, a condenser for separating the methane and water, and an electrolyzer for electrolyzing the water to hydrogen and oxygen.

4 Claims, 1 Drawing Sheet

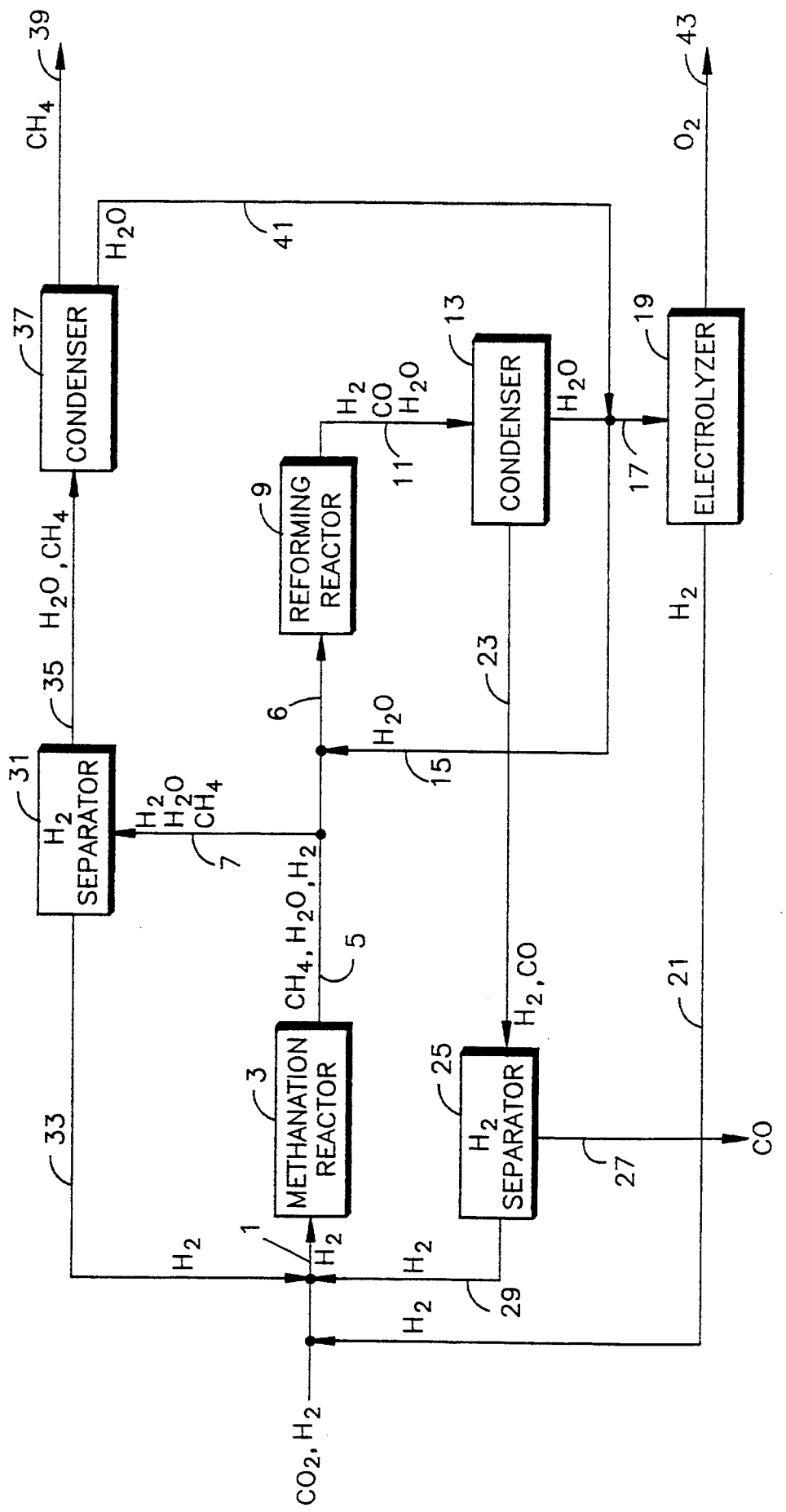

OXYGEN AND METHANE PRODUCTION DEVICE

This is continuation of Ser. No. 07/837,127 filed Mar. 13, 1992, now abandoned, which is a division of application Ser. No. 07/777,969 filed on Oct. 17, 1991, now U.S. Pat. No. 5,128,003.

TECHNICAL FIELD

The present invention relates to oxygen and methane production, and especially relates to the production of oxygen and methane from carbon dioxide and hydrogen.

BACKGROUND ART

In order for humans to successfully explore beyond the bounds of the Earth, it will be necessary to bring along oxygen for life support and fuel for power. Carrying a sufficient supply of fuel and oxygen for a direct, round trip flight to locations beyond the Moon, however, is not technically feasible since these substances significantly contribute to weight and volume penalties.

As a result, on location oxygen and methane production has been extensively investigated. As is described in U.S. Pat. No. 4,452,676 (incorporated herein by reference), oxygen and methane can be produced in an environment containing abundant amounts of carbon dioxide. Therefore, extraterrestrial bodies, such as asteroids and planets, possessing an abundance of carbon dioxide are potential oxygen and methane production sites. For example, carbon dioxide is indigenous to Mars, equaling about 95.3% of its atmosphere. Therefore, on location, methane and oxygen production can be accomplished on Mars.

The oxygen and methane production consists of converting carbon dioxide and hydrogen to methane and water vapor. The methane and water vapor are separated by cooling the methane and water vapor stream such that the water condenses. The condensed water is directed to an electrolyzer where it is electrolyzed to its constituents, hydrogen and oxygen. This hydrogen is recycled for additional conversion of carbon dioxide to water and methane. The oxygen can be stored for use as an oxidant for fuel or utilized for life support.

Meanwhile, the methane is separated into two portions. One portion of the methane is stored as fuel, while the remainder of the methane is introduced to a carbon formation reactor where it is pyrolyzed to its constituents, hydrogen and carbon. This hydrogen is similarly recycled as a reactant for the production of methane and water. The carbon, on the other hand, accumulates on expendable glass packing in the carbon formation reactor as solid carbon.

Although this oxygen and methane production process is an improvement over carrying methane and oxygen as cargo on extraterrestrial flights, limitations relating to the expendables significantly contribute to weight and volume penalties. Here, disposal of the solid carbon and replacement of expendables such as the glass packing are limitations which were not experienced by the prior art.

The methane produced from the carbon dioxide and hydrogen is pyrolyzed to hydrogen and solid carbon which deposits on the glass packing in the carbon formation reactor. Eventually, the accumulated solid carbon increases the pressure drop across the carbon formation reactor to a point where the energy requirements for passing the methane through the reactor become excessive, making further methane pyrolysis impractical. As a result, the solid carbon must be removed and disposed of or stored, and the glass packing must be cleaned or replaced.

Removal of the accumulated solid carbon is a manual procedure which requires cooling the carbon formation reactor to a temperature at which the carbon can be handled, about 45° C. (113° F.), disassembling the carbon formation reactor, physically removing the carbon from the reactor, and replacing the expendable glass packing with a new glass packing. Once the glass packing has been replaced, the reactor must then be reassembled and brought back up to temperature, about 1200° C. (2192° F.), thereby requiring an additional energy expenditure.

If the teachings of U.S. Pat. No. 4,452,676 are employed, oxygen and methane would not be required cargo in a flight to Mars. However, this process is limited in that it requires expendables such as glass packing and containers for storing the glass packing. For example, a return mission from Mars would require the production of 23 metric tons of methane. Such methane production would require 29 $m^3$ of glass packing for the 17.2 metric tons of carbon produced during pyrolysis. Although the glass packing consumes less volume and weight than carrying oxygen and methane as cargo, it fails to solve the volume and weight problems experienced by the prior art. Also, the carbon coated glass packing must be disposed of, creating a disposal problem.

What is needed in the art is an automated process for the production of oxygen and methane from carbon dioxide and hydrogen that is efficient, does not require expendables, and can be run in a continuous process.

DISCLOSURE OF THE INVENTION

The present invention is directed to a method for producing oxygen from carbon dioxide and hydrogen. Carbon dioxide and hydrogen react to form methane and water in a methanation reactor. Due to the stoichiometry of the above reaction, a greater amount of water than methane is produced. The water and methane produced are introduced to a reforming reactor where they produce hydrogen and carbon monoxide. Due to the stoichiometry of this reaction, excess water exits the reforming reactor after the conversion of the methane. This water is electrolyzed to its constituents, hydrogen and oxygen.

The present invention is further directed to a method for producing oxygen and methane from carbon dioxide and hydrogen. The carbon dioxide and hydrogen are introduced to a methanation reactor where they are reacted to produce methane and water. A first portion of the methane and water are directed to a reforming reactor where they react to form hydrogen and carbon monoxide. Meanwhile, a second portion of the methane and water are separated, and the water is directed to an electrolyzer. In the electrolyzer, the water is electrolyzed to hydrogen and oxygen.

The present invention is also directed to an apparatus for the production of oxygen and methane from carbon dioxide and hydrogen. This apparatus includes: a methanation reactor for converting carbon dioxide and hydrogen to methane and water, a reforming reactor for converting the methane and water produced in the methanation reactor to carbon monoxide and hydrogen, and an electrolyzer for electrolyzing the water to hydrogen and oxygen.

The foregoing and other features and advantages of the present invention will become more apparent from the following description an accompanying drawing.

BRIEF DESCRIPTION OF THE DRAWING

The FIGURE is a schematic of the oxygen and methane production process of the present invention.

BEST MODE FOR CARRYING OUT THE INVENTION

The FIGURE, which shows a schematic of one embodiment of the system disclosed in the present invention, is meant to be exemplary and not limiting. The methanation reactor 3 is a conventional piece of equipment capable of converting carbon dioxide and hydrogen to methane and water, such as the Sabatier methanation reactor.

In the methanation reactor 3, carbon dioxide ($CO_2$) and hydrogen ($H_2$) are converted to methane and water at elevated temperatures. Conversion of the carbon dioxide and hydrogen typically occurs on a catalyst composed of chromium, cobalt, nickel, noble metals, and others, with ruthenium preferred. The catalyst is typically at an elevated temperature which can be attained by either supplying heat to the reactor or exothermically reacting hydrogen and oxygen on the catalyst. Since the reaction (see Equation 1 below) is exothermic, it is self-sustaining once the reaction temperature has been attained. As a result, the methanation reactor 3 does not require continuous heating.

After the methanation reactor 3 has been heated, the reactants are introduced. These reactants are preferably filtered to remove particulates prior to entering the methanation reactor 3 to prevent catalyst contamination and increased pressure drop due to particulates becoming trapped within the catalyst bed.

In the methanation reactor 3, the carbon dioxide and hydrogen chemically react on the methanation catalyst at temperatures above about 120° C. (248° F.). This chemical reaction forms an effluent stream containing methane and water vapor according to the following exothermic reaction:

$$CO_2 + 4H_2 \rightleftharpoons CH_4 + 2H_2O \tag{1}$$

Temperatures below about 593° C. (1100° F.) are preferred since the reverse reforming reaction from methane and water to carbon dioxide and hydrogen is predominant at temperatures exceeding 593° C. (1100° F.). If the reforming reaction predominates, the oxygen and methane production and the overall system efficiency decreases.

Once the methanation reaction is complete, the effluent stream 5 from the methanation reactor 3 is directed to a reforming reactor 9 where the methane and water are converted to hydrogen and carbon monoxide. Typically, the reforming reactor 9 contains a reforming catalyst which is similar to the methanation catalyst discussed above and is capable of converting methane and water to hydrogen and carbon monoxide.

The reforming reactor 9 is maintained at elevated temperatures to influence the direction of the reaction within this reactor. Reaction temperatures above about 593° .C (1100° F.) are typically employed since below this temperature, the rate of reaction is severely diminished. Operating temperatures between about 800° C. (1472° F.) to about 1200° C. (2192° F.) are preferred due to improved reaction rates and conversion efficiencies at higher temperatures. Although temperatures up to about 1200° C. (2192° F.) can be used, temperatures below or about 1000° C. (1832° F.) are especially preferred due to possible material problems such as catalyst degradation at higher temperatures.

After the reforming reactor 9 has attained reaction temperatures, the methanation effluent stream 5 from the methanation reactor and a water stream 15 are introduced as inlet stream 6. Within the reforming reactor 9, the water and methane intimately contact the reforming catalyst, causing the water and methane to chemically react to form hydrogen and carbon monoxide according to the following endothermic reaction:

$$CH_4 + H_2O \rightleftharpoons 3H_2 + CO \tag{2}$$

If the entire effluent stream 5 is directed to the reforming reactor 9, the reforming reactor effluent stream 11 will contain excess water. As can be seen in Equation (2), the reforming reaction has a 1 to 1 methane to water stoichiometry. Since approximately twice as much water as methane is produced in the methanation reactor 3, Equation (1), there is excess water entering the reforming reactor 9. As a result, the reforming reactor effluent stream contains not only hydrogen and carbon monoxide, but also excess water.

The excess water in the reforming reactor effluent stream 11 is separated from the hydrogen and carbon monoxide by directing the stream to a conventional means for separating water from hydrogen and carbon monoxide, such as a first condenser 13. This condenser can utilize ambient gases (temperatures of about 25° C. (77° F.) on Earth and about −5° C. (44° F. ) on Mars), water based coolants, or other conventional coolants for cooling. Within this first condenser 13, the reforming reactor effluent stream 11 is cooled to below the water dew point to cause the water to condense. As a result, the hydrogen and carbon monoxide are separated from the water since the water exits the first condenser 13 as a liquid while the hydrogen and carbon monoxide exit in a separate stream as gases.

This hydrogen and carbon monoxide 23 are then directed to a first hydrogen separator 25 in order to separate the hydrogen from the carbon monoxide. The first hydrogen separator 25 is typically a membrane which allows the small hydrogen molecules to pass while rejecting the flow of carbon monoxide. Any conventional hydrogen separator capable of separating hydrogen from carbon monoxide can be used.

Generally, a solid metallic membrane fabricated from a silver-palladium alloy is used. This membrane preferentially dissolves hydrogen at elevated temperatures (about 300° C. (572° F.)) and rejects carbon monoxide. Similarly, nonporous polymeric membranes which preferentially pass hydrogen through its surface while rejecting the larger carbon monoxide molecules, can be employed. Matheson Gas Products, East Rutherford, N.J. is a supplier of the silver-palladium membrane separators while Permea, a Monsanto Company located in St. Louis, Mo., is a supplier of Prism ® polymeric membrane separators.

In the first hydrogen separator 25, the hydrogen passes through the membrane and exits the separator as stream 29 which can then be combined with the reactants in stream 1 or stored. The carbon monoxide is separated from this hydrogen since it cannot pass through this membrane. This carbon monoxide, stream 27, is either vented or stored.

Meanwhile, the condensed water which was separated from the hydrogen and carbon monoxide in the first condenser 13 exits the condenser. This water stream can be split such that a portion of the stream can be recycled as stream 15 and combined with the methanation effluent stream 5 for use in the reforming reactor 9. Recycling this water to the reforming reactor 9 is preferred since feeding water in excess of the stoichiometric requirement of 1 mole water to 1 mole methane results in improved conversion efficiency of methane to carbon monoxide and hydrogen in the reforming reactor 9.

While the first portion of the water stream is recycled, the second portion can be directed to an electrolyzer 19 for oxygen production. The electrolyzer 19 can be any conventional means for electrolyzing water, such as a SPE®, solid polymer electrolyte electrolysis cell produced by Hamilton Standard, Windsor Locks, Conn., or a conventional potassium hydroxide electrolyzer.

The SPE® electrolysis cell is preferred over the potassium hydroxide electrolyzer since the potassium hydroxide electrolyzer requires an additional step of scrubbing the inlet water stream to remove any carbon dioxide. The carbon dioxide can contaminate the potassium hydroxide reactor by converting the potassium hydroxide to potassium carbonate, thereby reducing the amount of potassium hydroxide available for water electrolysis. The SPE® electrolysis cell, in contrast, does not require the scrubbing of the water stream and is not contaminated by carbon dioxide.

After entering the electrolyzer 19, the water contacts a catalyst and is electrolyzed to its constituents, hydrogen and oxygen. This oxygen which exits the electrolyzer 19 in stream 43 can be stored or used for life support while the hydrogen can be directed via stream 21 to storage or combined with the reactants in stream 1.

A more effective utilization of the above described apparatus and process is a method in which the methanation effluent stream 5 is split into two streams; a first stream which is directed to the reforming reactor 9 as discussed above, and a second stream 7 which is separated into its constituents, methane and water. The methane can then be stored and utilized as a fuel while the water can be directed to the electrolyzer for electrolysis to hydrogen and oxygen.

Separation of the methane and water can be accomplished in any conventional means for separating water and methane, such as a second condenser 37 similar to the first condenser described above. The second stream 7 split from the methanation effluent stream 5, therefore, is directed to the second condenser 37 where the methane is separated from the water by cooling the stream to below the dew point of water. Since methane is insoluble in water, it is readily separated from the condensed water and directed to storage. The condensed water stream 41, on the other hand, can be directed to stream 17 to be combined with water condensed in the first condenser 13 or stored.

It is recognized that if there is any excess hydrogen in stream 7 from the reaction in the methanation reactor 3, it can be separated from the methane and water in a second hydrogen separator This second hydrogen separator 31 can be any conventional hydrogen separator capable of separating hydrogen from methane and water, such as a solid metallic membrane or a nonporous polymeric membrane, among others, as is discussed above with respect to the first hydrogen separator 25.

Once introduced to the second hydrogen separator 31, the hydrogen passes through a membrane which excludes the water and methane in stream 7. This hydrogen can be directed via stream 31 to storage or combined with the reactants in stream 1. Meanwhile, the water and methane excluded by the membrane can be directed via stream 35 to the second condenser 37 for additional separation as described above.

The following example is given to illustrate the continuous methane and oxygen production process of the present invention. It is not intended, however, to limit the generally broad scope of the present invention.

EXAMPLE

The following example describes a method for producing 3.0 kilograms per day of methane and oxygen, 0.6 kilograms per day of methane and 2.4 kilograms per day of oxygen. This represents the 4:1 oxygen to methane weight ratio that is desirable for stoichiometric combustion.

1. A methanation reactor 3 containing a ruthenium catalyst in a 20 cc catalyst bed is heated to 120° C. (248° F.) prior to the introduction of 4.95 kilograms per day (kg/day) of carbon dioxide, 0.15 kg/day of fresh hydrogen, 0.3 kg/day of recycled hydrogen from the electrolyzer 19, and 0.6 kg/day from the reforming reactor 9, and 0.075 kg/day of unreacted hydrogen 33 from the methanation reactor 3 are introduced into the methanation reactor 3. The inlet region of the methanation reactor 3 is maintained at 500° C. (932° F.) while the outlet is cooled to about 120° C. (248° F.) to maximize reactant conversion efficiency.
2. Hydrogen, 0.075 kg/day, 0.6 kg/day of methane, and 1.35 kg/day of water is removed from the effluent stream 5 from the methanation reactor 3. This represents 33% of the volumetric flow of the methanation reactor effluent 5.
3. The remainder of the effluent stream, 0.15 kg/day of hydrogen, 1.2 kg/day of methane, and 2.7 kg/day of water, is combined with an additional 2.7 kg/day of water 15 from a first condenser 13. This gives the 4:1 steam to methane ratio desired in the reforming reactor 9.
4. The combined inlet stream 6 is introduced to a reforming reactor 9 where the methane and water react to form hydrogen and carbon monoxide. reforming reactor effluent 11 contains 0.6 kg/day of hydrogen, 2.1 kg/day of carbon monoxide, and 4.05 kg/day of water. The reforming reactor 9 is maintained at 800° C. (1472° F.).
5. The reforming reactor effluent stream 11 is cooled in a first condenser 13 to less than 5° C. (41° F.) to condense the water out of stream 11.
6. A portion of the water 15, 2.7 kg/day, is combined with the reforming reactor inlet stream 6 while the hydrogen and carbon monoxide 23 are separated in a first hydrogen separator 25 such that the carbon monoxide 27 is vented and the hydrogen 29 is combined with the reactants 1.
7. Meanwhile, the stream 7 removed from the methanation effluent stream 5 is introduced to a second hydrogen separator 31 to separate the hydrogen from the methane and water. The separated hydrogen 33 is recombined with the reactants 1.
8. The water and the methane 35 are cooled in a second condenser 37 to 5° C. (41° F.) to condense out the water. The methane 39 is stored.

9. The water 41, 1.35 kg/day, is combined with 1.35 kg/day of the condensed water from the reforming reactor effluent 11.

10. The combined water 17 is introduced to an electrolyzer 19 where the water is electrolyzed to its constituents, hydrogen and oxygen. The hydrogen 21, 0.3 kg/day, is combined with the reactants 1, while the oxygen 43, 2.4 kg/day, is stored. The electrolyzer 19 is maintained at approximately 38° C. (100° F.) while 690 watts of energy is supplied to the electrolyzer 19 for the electrolysis process.

The present invention allows production of oxygen and methane on extraterrestrial bodies where carbon dioxide is abundant. The process is readily automated and continuous, requiring no manual removal of solids and no replacement of expendables. The present invention provides payload size and weight advantages over the prior art, and, therefore, will be particularly useful in advancing man's ability to explore boundless areas of space.

For example, the present invention renders production of oxygen and methane on Mars an efficient, continuous, gas phase process. The process disclosed is capable of producing oxygen and methane at any weight ratio greater than 2:1. Thus, it is possible to produce only oxygen and no methane. For the case of an oxygen to methane weight ratio of 3.5:1, the ideal mixture for maximizing specific impulse for propulsion, the leverage of fuel and oxidant produced to hydrogen supplied is 18:1.

The ability to produce variable amounts of oxygen and methane enables production to be based upon need. For example, if oxygen and methane production is merely for the return flight to earth, the weight ratio will be about 3.5:1. However, if additional oxygen is needed for life support, the weight ratio can change to about 4:1 or more, depending on the need. This ratio is varied by increasing or decreasing the flow of the methanation effluent stream directed to the reforming reactor. As the flow to the reforming reactor increases, the flow to the second condenser for separating methane and water decreases, and the amount of methane stored decreases.

The prior art required a payload of about 110 metric tons of fuel and oxidant to be carried as payload to Mars for the return flight. Compared to the prior art, the present invention realizes a weight savings of about 100 metric tons of payload which not only lightens the spacecraft, but decreases the necessary size of the spacecraft. It is assumed that approximately 2 metric tons of equipment is necessary for the on location production of oxygen and methane. Therefore, the cargo requirement is merely about 8 metric tons, 6 metric tons of hydrogen and about 2 metric tons of equipment.

Additionally, unlike U.S. Pat. No. 4,452,676, the present invention is not limited by expendables or the need to discard or store solid carbon. The present invention does not rely upon a carbon formation reactor to vary the oxygen to methane ratio, and therefore is not burdened with the problems thereof as discussed in the Background Art.

Although this invention has been shown and described with respect to detailed embodiments thereof, it will be understood by those skilled in the art that various changes in form and detail thereof may be made without departing from the spirit and scope of the claimed invention.

We claim:

1. A device for producing oxygen and methane, which comprises:
   a. a methanation reactor constructed and arranged for reacting carbon dioxide and hydrogen to produce methane and water;
   b. a reforming reactor in flow communication with said methanation reactor, wherein said reforming reactor contains a reforming catalyst and is constructed and arranged for reforming water and methane to produce hydrogen and carbon monoxide and wherein said reforming reactor is constructed for reaching and maintaining temperatures ranging from about 593° C. to about 1200° C.;
   c. a means for separating methane and water in flow communication with said methanation reactor; and
   d. an electrolyzer in flow communication with said means for separating, wherein said electrolyzer is constructed and arranged for electrolyzing water to hydrogen and oxygen.

2. A device as in claim 1 further comprising:
   a. a means for separating hydrogen and oxygen in flow communication with said electrolyzer; and
   b. a means for separating hydrogen and carbon monoxide in flow communication with said reforming reactor; wherein said means for separating hydrogen and oxygen and said means for separating hydrogen and carbon monoxide are further in flow communication with said methanation reactor.

3. A system for producing oxygen and methane, consisting essentially of:
   a. a methanation reactor for reacting carbon dioxide and hydrogen to produce methane and water;
   b. a reforming reactor containing a reforming catalyst in flow communication with said methanation reactor, for reforming water and methane to hydrogen and carbon monoxide wherein said reforming reactor is constructed for reaching and maintaining temperatures ranging from about 593° C. to about 1200° C.
   c. a means for separating methane and water in flow communication with said methanation reactor;
   d. an electrolyzer in flow communication with said means for separating methane and water for electrolyzing water to hydrogen and oxygen;
   e. a means for separating hydrogen and oxygen in flow communication with said electrolyzer; and
   f. a means for separating hydrogen and carbon monoxide in flow communication with said reforming reactor.

4. A system for producing oxygen and methane as in claim 3, wherein said system is constructed such that
   a. said methanation reactor is connected to said reforming reactor thereby allowing a portion of said methane and said water produced in said methanation reactor to be reformed to hydrogen and carbon monoxide,
   b. said methanation reactor is also connected to said means for separating methane and water thereby allowing a second portion of methane and water produced in said methanation reactor to be separated,
   c. said reforming reactor is connected to said means for separating hydrogen and carbon monoxide, thereby allowing the separation of said reformed hydrogen and reformed carbon monoxide,
   d. said means for separating methane and water is connected to said electrolyzer thereby allowing said separated water to be electrolyzed to hydrogen and oxygen,
e. said electrolyzer is connected to said means for separating hydrogen and oxygen, thereby allowing the separation of said electrolyzed hydrogen and electrolyzed oxygen, and
f. said means for separating hydrogen and oxygen and said means for separating hydrogen and carbon monoxide are connected to said methanation reactor, thereby allowing said separated reformer hydrogen and said separated electrolyzer hydrogen to be recycled to said methanation reactor.

* * * * *